United States Patent
Zahnow et al.

(10) Patent No.: US 10,272,403 B2
(45) Date of Patent: Apr. 30, 2019

(54) MIXING DEVICE HAVING A FLOW BREAKER

(71) Applicant: Sartorius Stedim Biotech GmbH, Goettingen (DE)

(72) Inventors: Christian Zahnow, Goettingen (DE); Sebastian Ruhl, Fulda (DE); Gerhard Greller, Goettingen (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 0 days.

(21) Appl. No.: 15/529,256

(22) PCT Filed: Oct. 20, 2015

(86) PCT No.: PCT/EP2015/074263
§ 371 (c)(1),
(2) Date: May 24, 2017

(87) PCT Pub. No.: WO2016/087113
PCT Pub. Date: Jun. 9, 2016

(65) Prior Publication Data
US 2017/0259231 A1    Sep. 14, 2017

(30) Foreign Application Priority Data
Dec. 2, 2014 (DE) .......... 10 2014 117 658

(51) Int. Cl.
*B01F 15/00* (2006.01)
*C12M 1/00* (2006.01)
(Continued)

(52) U.S. Cl.
CPC .......... *B01F 15/0085* (2013.01); *B01F 7/20* (2013.01); *B01F 15/00896* (2013.01);
(Continued)

(58) Field of Classification Search
CPC .............. B01F 15/0085; B01F 15/00915
(Continued)

(56) References Cited

U.S. PATENT DOCUMENTS 2,797,903 A * 7/1957 Urban ............... B01F 15/00837
217/53
7,547,135 B2    6/2009 Kocienski
(Continued)

FOREIGN PATENT DOCUMENTS

DE    202007005868 U1    7/2007
JP    2014-121302 A      7/2014
(Continued)

OTHER PUBLICATIONS

Office Action dated Aug. 3, 2015 by the German Patent and Trademark Office in German Priority Application No. 10 2014 117 658.8 filed Dec. 2, 2014.
(Continued)

*Primary Examiner* — David L Sorkin
(74) *Attorney, Agent, or Firm* — Dilworth IP, LLC

(57) ABSTRACT

A mixing device (10) comprises a flexible container (14), at least one stirring element (22) and at least one baffle (24). The baffle (24) is formed on the inside on a circumferential side wall (16) of the flexible container (14) and has a free end protruding into the interior of the container (14). A main application of the mixing device (10) is considered to be the use as disposable bioreactor.

16 Claims, 2 Drawing Sheets

(51) Int. Cl.
  *C12M 1/06* (2006.01)
  *B01F 7/20* (2006.01)
  *C12M 1/02* (2006.01)
(52) U.S. Cl.
  CPC ............ *C12M 23/26* (2013.01); *C12M 27/02* (2013.01); *C12M 27/20* (2013.01); *C12M 1/02* (2013.01)
(58) Field of Classification Search
  USPC .................................................. 366/275, 307
  See application file for complete search history.

(56) References Cited

U.S. PATENT DOCUMENTS

| | | | | |
|---|---|---|---|---|
| 7,629,167 | B2* | 12/2009 | Hodge | ................ B01F 13/0827 366/274 |
| 8,500,322 | B2 | 8/2013 | Morrissey et al. | |
| 2004/0062140 | A1* | 4/2004 | Cadogan | ................... B01F 7/18 366/144 |
| 2008/0151683 | A1* | 6/2008 | Meadows | ........... B01F 13/0818 366/145 |
| 2008/0151686 | A1* | 6/2008 | Meadows | ........... B01F 13/0818 366/274 |
| 2009/0314666 | A1* | 12/2009 | Reif | .................... B01F 15/0085 206/221 |
| 2010/0015696 | A1* | 1/2010 | Claes | .................. B01F 3/04269 435/303.3 |

FOREIGN PATENT DOCUMENTS

| | | |
|---|---|---|
| WO | 2005/118771 A2 | 12/2005 |
| WO | 2007/124847 A1 | 11/2007 |
| WO | 2007/134267 A2 | 11/2007 |
| WO | 2009/074213 A1 | 6/2009 |
| WO | 2014/003640 A1 | 1/2014 |
| WO | 2014/172047 A1 | 10/2014 |

OTHER PUBLICATIONS

PCT International Search Report dated May 2, 2016 in corresponding Application No. PCT/EP2015/074263.

\* cited by examiner

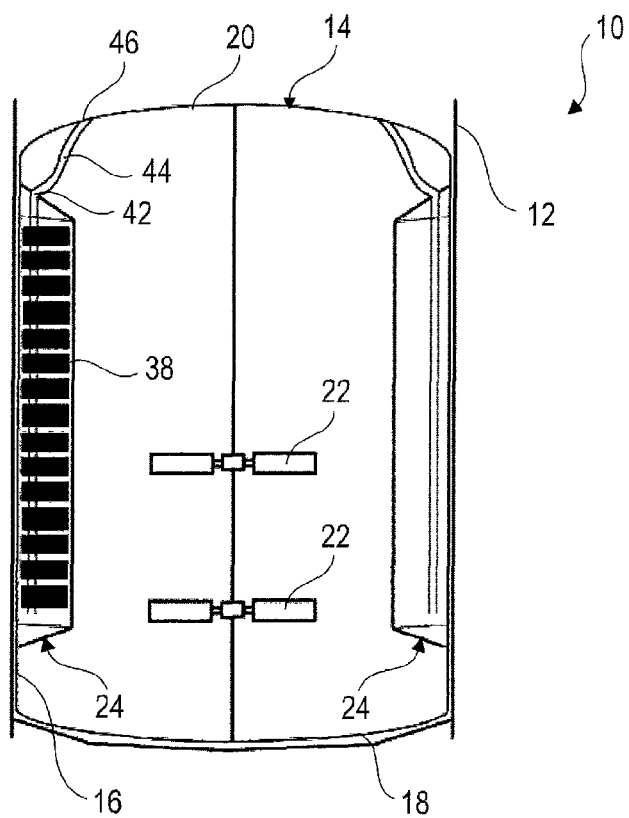
Fig. 1
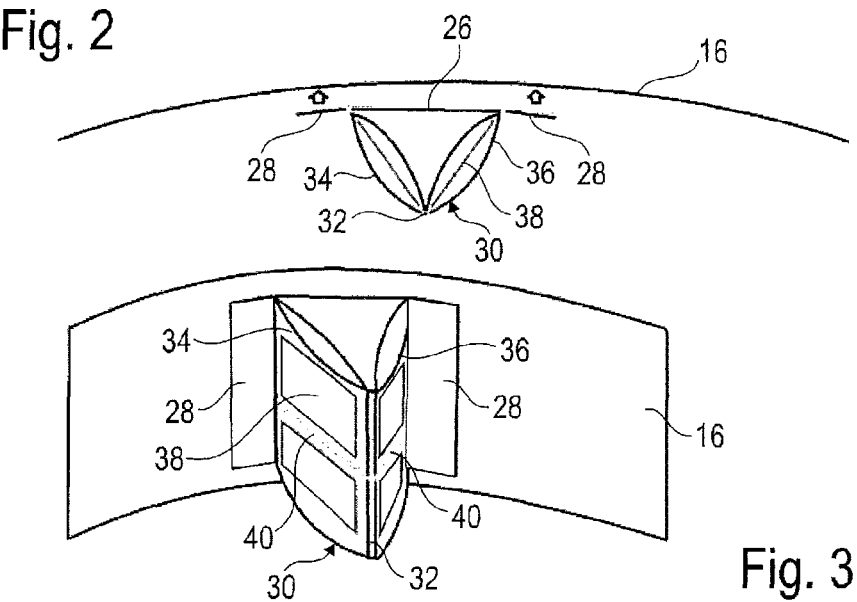
Fig. 2
Fig. 3

MIXING DEVICE HAVING A FLOW BREAKER

This invention relates to a mixing device with a flexible container and at least one stirring element as well as at least one baffle.

Mixing devices are used in various technical fields. Without limiting the invention reference will be made below to the use of mixing devices as bioreactors, in which certain microorganisms or vegetable or animal cells are to be cultivated under the best possible conditions.

BACKGROUND OF THE INVENTION

One type of bioreactor to be found frequently is the stirred tank with a rigid container, which mostly is formed of stainless steel, more rarely of glass or glass-fiber-reinforced plastics. A stirrer with one or more stirring elements arranged in the container ensures intermixing of the liquid present in the container. When adding substances to the liquid present in the container, such as a correcting agent, a fast and uniform distribution is desirable. The same applies in the case of gassing of the liquid; the introduced gas bubbles also should be kept in the liquid as long as possible.

To prevent the formation of clots which occur during stirring when the liquid present in the container rotates with the container, and to produce an increased turbulence, obstacles in the form of flow spoilers, so-called baffles, can be mounted on the container wall. These components protruding into the container "disturb" the uniform course of the flow of the liquid in the container and thereby can considerably improve intermixing. With regard to the cultivation of microorganisms in bioreactors, the baffles provide for distinctly higher stirring speeds. This in turn allows an increased input of oxygen into the liquid, which is indispensable for this kind of cultivation.

An example for a stirred tank with baffles radially protruding from the rigid container wall can be found in U.S. Pat. No. 7,547,135 B2.

To avoid the sterilization effort before on-site use of a bioreactor, pre-sterilized disposable containers with flexible walls are used to an increased extent. These bag-like containers can be folded together for transport in a space-saving way and before use generally are inserted into a support container, although other supporting structures for holding the disposable containers partly filled with very large amounts of liquid also are known. Pre-sterilized disposable containers already can be equipped with a plurality of pre-mounted hoses. In addition, pre-sterilized stirring elements can be integrated into the bags, which e.g. via magnetic bodies in the interior of the bag are coupled with an external stirrer motor of the bioreactor.

From WO 2005/118771 A2 and WO 2007/124847 A1 container assemblies as mentioned above are known. To improve the mixing operation, there are also provided baffles which are mounted on the inner wall of the support container. The lateral wall of the flexible disposable container clings to the inner wall of the support container with the integrally molded baffles, so that the baffles—covered by the wall of the disposable container—can fulfill their function.

This solution has the advantage that the disposable container can be of simple design, as it need not be provided with baffles itself, and that the baffles of the support containers can be used again and again. The number, arrangement and shape of the baffles at the support container however are fixed and cannot be varied. It must also be noted that the wall of the disposable container is greatly deformed at the baffles and therefore is exposed to a great load. Another disadvantage of this construction consists in that the baffles reduce the effective bearing surface of the disposable container wall on the inner wall of the support container, which renders a dissipation of heat from the disposable container to the support container more difficult.

A similar construction of a container assembly like in the above-mentioned documents WO 2005/118771 A2 and WO 2007/124847 A1 also is shown in WO 2009/074213 A1. Here, the baffles at the support container additionally can be equipped with a tempering system, in order to promote uniform and fast tempering. For this purpose, the baffles include parallel tubes through which a liquid can be passed with a specified temperature.

Another alternative to the provision of baffles when using a disposable container would be shrink-wrapping of a rigid plastic part into the flexible bag. However, due to the transport of the disposable container in the compressed condition this is not possible or at least not possible without loss of space and additional safety measures.

U.S. Pat. No. 8,500,322 B2 proposes a mixing device with a plastic bag which is inserted into a rigid support container and includes a baffle in the form of a perforated film web. The film web extends between at least two inner surfaces of the bag, such as from the upper to the lower surface or between two lateral surfaces. The film web hence always traverses the entire bag. The perforation only partly allows the liquid put into motion by the stirrer to flow through the film web.

From WO 2014/172047 A1 there is furthermore known a disposable bioreactor with a flexible baffle, which includes two intersecting legs. The ends of the baffle all are attached to the inner wall of the bioreactor.

JP 2014-121302A shows a cell culture container with a stirrer and a baffle made of plastics, which in the container extends in direction of the stirrer axis. The baffle is inserted between two opposed vertically extending edges of two film portions from which the main container portion is formed. The fixation of the baffle at the film edges is effected by welding (heat sealing). The stability of this fixation however is limited. The baffles are provided with holes through which the substance to be cultivated can pass. Due to the shear forces produced thereby, the holes can turn out to be unfavorable for biological material. The use of perforated baffles preferably should be seen in media with microcarrier cell cultures.

BRIEF SUMMARY OF THE INVENTION

It is the object of the invention to provide for a material-saving, variably specifiable arrangement of baffles for optimum intermixing in a mixing device with a flexible container.

This object is solved by a mixing device with the features of claim 1. Advantageous and expedient aspects of the mixing device according to the invention are indicated in the sub-claims.

The mixing device according to the invention comprises a flexible container, at least one stirring element and at least one baffle. The baffle is formed (mounted or integrally molded) on the inside on a circumferential side wall of the flexible container and has a free end protruding into the interior of the container.

The invention is based on the finding that a baffle which is formed on the inside of the flexible container and freely protrudes into the container (i.e. does not extend completely up to an opposite side of the container like in U.S. Pat. No.

8,500,322 B2) can be stabilized by suitable measures such that it can exert the desired function, namely a targeted improvement of intermixing, in the same way as a baffle firmly mounted on a rigid container. Care should merely be taken that the fixing points of the baffle according to the invention are stable enough to exclude tearing out. With a suitable design of the baffle such stable connections can be realized by welding or gluing, but without any major problems.

The concept underlying the invention provides for the largest possible flexibility with regard to the number, arrangement and shape of the baffles, as they can be designed and mounted individually depending on the requirement. Firmly installed baffles do not offer such adaptability.

The baffles of the mixing device according to the invention possibly can be provided separately, so that it can be decided only at the site of use which and how many baffles are mounted where on the flexible container of the mixing device. In the case of pre-sterilized flexible disposable containers the same are offered pre-assembled, i.e. the baffles are mounted already, before the flexible containers are dispatched. The advantage here is that even with the mounted baffles the flexible container still can very easily be folded together to form a compact package.

Another essential advantage of the invention, in particular as compared to solutions with bags which are inserted into support containers with integrally molded baffles, consists in that the flexible container is not exposed to any excessive mechanical loads. As the flexible container of the mixing device according to the invention itself carries the baffles, it need not be deformed by external baffles of the support container. The flexible container rather can uniformly rest against the inner walls of the support container, which results in a better heat transfer between the flexible container and the support container.

According to a preferred embodiment of the mixing device according to the invention, the baffle preferably has a shell which is formed of a flexible film material. The flexibility of the shell facilitates folding together for transport. For use as baffle rigid elements either are inserted into the shell and/or a fluid (liquid or gas) is introduced, which at least contributes to the dimensional stabilization of the baffle. Both possibilities will be discussed in more detail below. The flexible shell thus can be brought into a desired shape or be stabilized in a desired shape.

The shell of the baffle preferably includes a double-layered portion. In such portion cavities or compartments for accommodating rigid elements or a fluid easily can be formed.

According to the preferred aspect of the baffle the shell, in particular its double-layered portion, is divided into two receiving portions by means of a vertical partition, wherein the vertical partition protrudes into the interior of the container as a free end of the baffle. (The term "vertical" relates to the position of use of the mixing device.) In this aspect—expressed in a geometrically simplified way—the shell forms the side faces of a straight prism with a triangle as base area. This basic shape of the baffle has proved its worth and can be adapted to the respective requirements by varying the side lengths and angles.

As mentioned already, rigid elements can be inserted into the shell, in order to ensure the required stability of the baffle. It is recommendable to arrange at least one dimensionally stabilizing plate in the shell. Material, shape and thickness of the plate can appropriately be chosen in dependence on the respective requirements and the dimensions of the shell.

According to a development of the invention the shell includes several partitioned compartments, in each of which a plate is accommodated. This design is based on the advantage that several small plates are easier to handle than one large one. Moreover, in use of several small plates the baffle can be folded together in a more compact form. "Partitioned compartments" here should be mean that a plate cannot slip out of its compartment on its own, so that the position of the respective plate is fixed during operation.

Alternatively or in addition to the plates, the shell or the entire baffle can be brought into the desired shape and/or be stabilized further by filling with a fluid. It therefore is provided that the shell or the entire baffle is sealed in a gas-tight way and includes at least one fluid port.

A particularly advantageous design variant is obtained when the shell or the entire baffle is sealed in a gas-tight way and includes two fluid ports which preferably are arranged at vertically opposite ends of the shell or baffle. Such construction allows to continuously let a tempered fluid flow through the shell protruding into the interior of the container and/or through the entire baffle. In this way, the liquid in the interior of the container can be brought to a desired temperature and can be kept at this temperature.

The two effects "shaping/stabilization by fluid" and "tempering by fluid" can easily be combined with each other, in the most favorable case by using the same fluid ports.

For fixing the baffle at a wall of the flexible container (side wall, bottom wall, ceiling wall) the baffle according to a preferred embodiment of the invention includes two tabs. The same can be connected with the corresponding wall of the flexible container face to face, in particular by welding or gluing, so that upon introduction of the forces acting on the baffle onto the flexible container no force peaks threatening the stability will occur.

An advantageous design in this connection provides that the tabs extend on opposite sides of a base portion facing the shell. In the ideal case, a symmetrical fixation thereby is achieved on both sides of the shell.

Mounting the baffles on the flexible container by welding or gluing is easiest when identical materials are connected with each other. Therefore, the flexible container and the tabs preferably are formed of the same material. When the remaining parts of the baffle, in particular the shell (with the exception of rigid elements possibly accommodated therein or possibly existing tube connections and lines), also are formed of the same material, the manufacture of the baffle is simplified further.

For particular applications it is advantageous that the liquid present in the container can flow through between the inside of the flexible container and the baffle. This can be achieved by correspondingly arranged spacers. An arrangement of the baffle spaced from the inner wall can provide additional fluidizations and turbulences with regard to even better intermixing.

This behavior can further be influenced by the size and the space between vertically and/or horizontally spaced spacers.

The baffle provided according to the invention preferably has no through openings, so that no shear forces unfavorable for biological material can be produced.

BRIEF DESCRIPTION OF THE SEVERAL VIEWS OF THE DRAWING

Further features and advantages of the invention can be taken from the following description and from the attached drawings, to which reference is made. In the drawings:

FIG. 1 shows a lateral sectional view of a mixing device with baffles according to the invention;

FIG. 2 shows a top view of a segment of a mixing device according to the invention;

FIG. 3 shows a perspective view of a segment of a mixing device according to the invention.

DETAILED DESCRIPTION OF THE INVENTION

Figure 4:
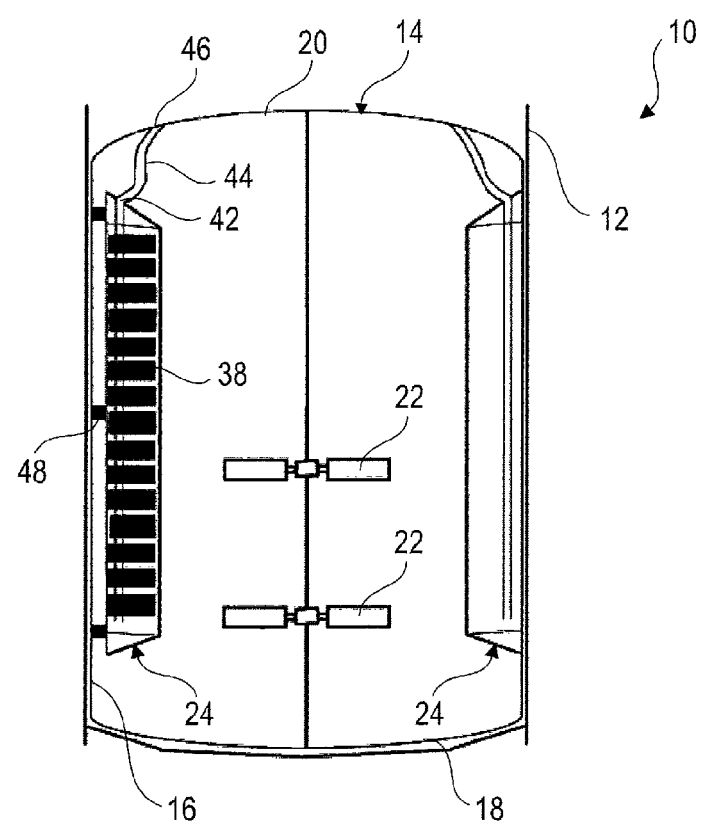
FIG. 4 shows a lateral sectional view of a mixing device with a baffle according to the invention in a design variant with spacers.

FIG. 1 shows a mixing device 10 which is provided for use as bioreactor. The mixing device comprises a substantially cylindrical support container 12 open at the top, into which a container 14 with flexible walls 16, 18, 20 is inserted. The flexible container 14 is arranged such that its walls, in particular the circumferential side wall 16 and the bottom wall 18, rest against the opposed inner walls of the support container 12 as far as possible with regard to an optimum support and an optimum heat transfer.

The flexible container 14 here is a culture vessel in the form of a pre-sterilized disposable bag which is formed of a film. Into the flexible container 14 two stirring elements 22 are integrated, which are parts of a stirrer of the mixing device 10. There can of course also be provided another number of stirring elements 22.

On the inside of the circumferential side wall 16 of the flexible container 14 several baffles 24 are mounted, which extend into the interior of the container. The construction and installation of the baffles 24 will be explained in detail below with reference to the exemplary representation of a baffle 24 in FIGS. 2 and 3.

The baffle 24 for the most part is formed of a film which preferably consists of the same material as the flexible container 14. From a base portion 26 two tabs 28 extend on opposite sides, by means of which the baffle 24 is fixed at the side wall 16 of the flexible container 14, in particular by welding.

Between the tabs a shell 30 furthermore extends in the form of a double-layered film portion which is welded to the tabs 28 or connected with the same in some other way or integrally formed with the same. The double-layered portion in turn is divided into two receiving portions 34, 36 by a middle vertical partition 32, for example a welding seam. In the position of use of the mixing device 10 as seen from above (see FIG. 2) the two receiving portions 34, 36 and the base portion 26 together form a triangle whose tip, represented by the vertical partition 32, protrudes into the interior of the container as free end of the baffle 24.

Into the receiving portions 34, 36 rigid plates 38 are inserted. The receiving portions 34, 36 are divided by a plurality of substantially horizontal partitions 40, for example welding seams, such that several compartments are formed. In each of these compartments a plate 38 is accommodated.

The baffles 24 alone can be spread out flat or be folded together for transport in a space-saving way, even if the plates 38 already are inserted. The assembly of the baffles 24 at the flexible container 14 then can be effected at the site of use, in that the prefabricated baffles 24 are mounted on the flexible container 14 at the desired points.

In pre-sterilized disposable containers on the other hand it is provided to install the baffles 24 already before shipment of the mixing device 10, in particular when a particular configuration frequently is desired, for example with four identical baffles uniformly distributed around the inner circumference of the flexible container 14. In this case, the flexible container 14 still can be folded together to form a relatively compact package.

In the following some design variants of the mixing device 10 will be described with reference to the baffles 24. It generally applies that not all features of a particular design variant necessarily must be realized. On the other hand, features of different design variants also can be combined with each other.

To bring a baffle 24 into its final shape, the same can be filled with a liquid or a gas (hereinafter: fluid) alternatively or in addition to the plates 38. For this purpose, as indicated in FIG. 1, the baffle 24 is equipped with at least one fluid port 42 which via a hose line 44 can be connected with a fluid port 46 arranged in the ceiling wall 20 of the flexible container 14. Otherwise, the baffle 24 is sealed in a gas-tight way.

As far as necessary, the distribution of the supplied fluid within the baffles 24 is effected via further hose lines or other flow connections between the compartments in which the plates 38 are accommodated. Just as well, however, separate portions in the baffles 24 or the entire baffles 24 also can be provided to take up the fluid. As mentioned already, the reinforcing plates 38 also can be omitted partly or entirely in the case of a fluid stabilization, as is indicated in the right-hand half of FIG. 1.

In general, the pressure which is introduced by the fluid must not endanger the stability of the baffles 24, in particular of the partitions 32, 40 (welding seams)—as far as present—and the fixing points. In practice, the maximum admissible pressure largely depends on the used film material.

Alternatively or in addition, the supplied fluid can be utilized for tempering the flexible container 14 or the liquid present therein. In this case, an additional fluid port is provided at the shell 30 or at another wall delimiting the interior space of the baffle 24, through which the fluid can again be guided out of the baffle 24 at another point, so that a continuous flow of tempered fluid through the baffle 24 is possible. Of course, separate hose lines or the like also can be provided for this purpose.

Since the fluid flowing into or through the baffle 24 does not get in contact with the sensitive content of the flexible container 14, a non-sterile fluid (e.g. ambient air or normal water) can be used for the above-mentioned purposes. Alternatively, a filter also can be connected before the supplied fluid, in order to guide the same into or through the baffles in a sterile condition.

A further design variant is shown in FIG. 4. Here, several spacers 48 are arranged between the side wall 16 of the flexible container 14 and a baffle 24. In this arrangement, the liquid in the flexible container 14—as seen vertically—can flow through between the spacers 48. In conjunction with the impenetrable baffles 24 further fluidizations can be enforced and intermixing thereby can be promoted. The radial distance of the baffles 24 from the side wall 16 of the flexible container 14, which is achieved by means of the spacers 48, lies in a range between 0 and about 200 mm in dependence on the container size.

Apart from the baffles 24 on the side wall 16 of the flexible container 14, baffles in principle can also be arranged on the bottom wall 18 and/or on the ceiling wall 20.

As already mentioned above, the invention is not limited to disposable bioreactors, but can also be used in other bag-based mixing devices.

LIST OF REFERENCE NUMERALS

10 mixing device
12 support container 14 flexible container
16 side wall
18 bottom wall
20 ceiling wall
22 stirring element
24 baffle
26 base portion
28 tab
30 shell
32 vertical partition
34 receiving portion
36 receiving portion
38 plate
40 horizontal partition
42 fluid port
44 hose line
46 fluid port
48 spacer

The invention claimed is:

1. A mixing device comprising a flexible container, at least one stirring element and at least one baffle, wherein the baffle is formed on the inside on a circumferential side wall of the flexible container and has a free end protruding into the interior of the container, wherein the baffle has a shell which is formed of a flexible film material and comprises a double-layered portion wherein the double-layered portion of the shell is divided into two receiving portions by means of a vertical partition, wherein the vertical partition protrudes into the interior of the container as a free end of the baffle.

2. A mixing device comprising a flexible container, at least one stirring element and at least one baffle, wherein the baffle is formed on the inside on a circumferential side wall of the flexible container and has a free end protruding into the interior of the container, wherein the baffle has a shell which is formed of a flexible film material, characterized in that at least one dimensionally stabilizing plate is arranged in the shell.

3. The mixing device according to claim 1, characterized in that the shell comprises several partitioned compartments, in each of which a plate is accommodated.

4. The mixing device according to claim 1, characterized in that the shell or the entire baffle is sealed in a gas-tight way and includes at least one fluid port.

5. A mixing device comprising a flexible container, at least one stirring element and at least one baffle, wherein the baffle is formed on the inside on a circumferential side wall of the flexible container and has a free end protruding into the interior of the container, wherein the baffle has a shell which is formed of a flexible film material, wherein the shell or the entire baffle is sealed in a gas-tight way and includes at least one fluid port, wherein the shell or the entire baffle is filled with a tempered fluid.

6. A mixing device comprising a flexible container, at least one stirring element and at least one baffle, wherein the baffle is formed on the inside on a circumferential side wall of the flexible container and has a free end protruding into the interior of the container, wherein the baffle comprises two tabs for fixing the baffle at the circumferential side wall of the flexible container.

7. The mixing device according to claim 6, characterized in that the tabs are fixed at the circumferential side wall by welding or gluing.

8. The mixing device according to claim 6, characterized in that the baffle has a shell formed of a flexible film material and the tabs extend on opposite sides of a base portion facing the shell.

9. The mixing device according to claim 6, characterized in that the flexible container and the tabs are formed of the same material.

10. The mixing device according to claim 1, characterized in that between the inside of the flexible container and the baffle several spacers are arranged.

11. The mixing device according to claim 10, characterized in that the spacers are spaced from each other vertically and/or horizontally.

12. The mixing device according to claim 1, characterized in that the baffle has no through openings.

13. The mixing device according to claim 2, characterized in that the shell includes several partitioned compartments, in each of which a plate is accommodated.

14. The mixing device according to claim 2, characterized in that the shell or the entire baffle is sealed in a gas-tight way and includes at least one fluid port.

15. The mixing device according to claim 1, characterized in that the flexible container and the shell are formed of the same material.

16. The mixing device according to claim 2, characterized in that the flexible container and the shell are formed of the same material.

* * * * *